(12) United States Patent
Chow et al.

(10) Patent No.: US 8,232,446 B2
(45) Date of Patent: Jul. 31, 2012

(54) NON-HUMAN ANIMAL MODEL FOR LUNG CARCINOMA

(75) Inventors: Yen-Hung Chow, Miaoli County (TW); Shih-Yang Hsieh, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 277 days.

(21) Appl. No.: 12/695,645

(22) Filed: Jan. 28, 2010

(65) Prior Publication Data

US 2010/0235927 A1 Sep. 16, 2010

Related U.S. Application Data

(60) Provisional application No. 61/160,637, filed on Mar. 16, 2009.

(51) Int. Cl.
*G01N 33/574* (2006.01)
*A01K 67/027* (2006.01)

(52) U.S. Cl. ............................................. 800/3; 800/10

(58) Field of Classification Search ........................ None
See application file for complete search history.

(56) References Cited

OTHER PUBLICATIONS

Dakessian et al (Virus Genes 2007; 35: 73-80).*
Taketo et al. (PNAS. 1991; vol. 88, pp. 2065-2069).*
Ebenezer Chitra, Shu-Ling Yu, Kuang-Nan tisiao, Hsiao-Yun Shao, Charles Sia, I-Hue Chen, Shih-Yang Hsieh, Jen-Hao Chen, Yen-Hung Chow (2009) "Generation and characterization of JSRV envelope transgenic mice in FVB background" Virology 393: 120-126.
Dakessian RM, Inoshima Y, Fan H. (2007) "Tumors in mice transgenic for the envelope protein of Jaagsiekte sheep retrovirus." Virus Genes 35(1):73-80.
Wootton SK, Halbert CL, Miller A. D. (2005) "Sheet retrovirus structural protein induces lung tumours" Nature 434: 904-907.

* cited by examiner

*Primary Examiner* — Scott Long
(74) *Attorney, Agent, or Firm* — Hsiu-Ming Saunders; Intellectual Property Connection, Inc.

(57) ABSTRACT

A transgenic mouse expressing JSRV Env transgene that is operably linked to a surfactant protein C promoter (SPCp) is disclosed. The transgenic mouse is prone to developing a lung tumor and serves as an animal model for human lung carcinoma.

20 Claims, 9 Drawing Sheets

CCSP

Env

NON-HUMAN ANIMAL MODEL FOR LUNG CARCINOMA

REFERENCE TO RELATED APPLICATION

The present application claims the priority to U.S. Provisional Application Ser. No. 61/160,637, filed Mar. 16, 2009, which is herein incorporated by reference in its entirety.

FIELD OF THE INVENTION

The present invention relates generally to transgenic animal model, and more specifically to a transgenic animal model for lung carcinoma.

BACKGROUND OF THE INVENTION

Jaagsiekte sheep retrovirus (JSRV) is the causative agent of ovine pulmonary carcinoma (OPC), a contagious lung cancer of sheep. JSRV-induced OPC consists of transformed secretary epithelial cells of the lungs: type II pneumocytes and Clara cells. A characteristic feature of OPC tumors is the production of large amounts of fluid secreted from the tumor cells containing infectious virus. OPC closely resembles human brochioloalveolar carcinoma (BAC), an adenocarcinoma not associated with cigarette smoking and whole etiology is currently unknown. Thus, OPC is an important model for understanding human BAC pathogenesis.

The JSRV envelope (Env) is a type-I transmembrane protein that has approximately 620 amino acids. The mature full-length Env is composed of a surface domain (SU) and transmembrane (TM) domain linked by disulfide bonds. The JSRV Env protein serves a function of binding virions to the cell surface viral receptor, and also functions as an oncogene. Miller et al. reported that expression of the JSRV Env protein alone in the lungs of mice by using a replication-incompetent adeno-associated virus vector resulted in tumors with a bronchiolo-alveolar localization like those seen in sheep. According to Woottn et al., the tumors were lethal to immunodeficient mice, however, tumor development was almost entirely blocked in immunocompetent mice (Wootton et al. (2005) "Sheep retrovirus structural protein induces lung tumours" *Nature* 434: 904-907). Wootton et al. did not establish any transgenic mouse carrying JSRV Env in germ cell lines.

Dakessian et al. microinjected a DNA construct containing surfactant protein C (SPC) promoter driven JSRV Env (SPC-Env) into fertilized eggs and implanted the eggs into pseudopregnant foster mother (Dakessian et al., (2007) "Tumors in mice transgenic for the envelope protein of Jaagsiekte sheep retrovirus." *Virus Genes* 35(1):73-80). They were not able to obtain transgenic mice from the SPC-Env DNA construct and thus concluded that the transgene SPC-Env was lethal to embryos. They switched to a transgene expressing an epitope-tagged JSRV Env under the control of the lung-specific surfactant protein A (SPA) promoter and were able to generate transgenic F1 mice containing SPA-Env-HA transgene showing low efficiency but specific expression in the lung. According to Dakessian et al., only one out of 22 founders gave rise to transgenic F1 progeny that developed tumors in the lung but that founder itself did not develop any tumors. Their transgenic mice had limitations in developing experimental animal model due to the difficulties in maintenance and breeding.

Therefore, a previously unaddressed need exists in the art to address the aforementioned deficiencies and inadequacies, especially in connection with development of an animal model for lung carcinoma.

SUMMARY OF THE INVENTION

In one aspect, the invention relates to a transgenic mouse whose genome comprises a JSRV Env transgene operably linked to a surfactant protein C promoter (SPCp), wherein the lung tissue of the mouse expresses the JSRV Env transgene, and wherein the mouse is prone to developing a lung tumor.

In another aspect, the invention relates to a transgenic mouse whose genome comprises a JSRV Env transgene operably linked to a type II pneumocyte-specific promoter, wherein the JSRV Env transgene is devoid of an untranslated long term repeat region at 3' end thereof, and wherein the mouse is prone to developing a lung tumor. The JSRV Env transgene has no HA tag.

In one embodiment of the invention, the aforementioned transgenic mouse is characterized by having more than 5% of chance to develop a lung tumor by the age of 1 month, or having more than 8% of chance to develop a lung tumor by the age of 3 months, or having more than 10% of chance to develop a lung tumor by the age of 7 months.

In another embodiment of the invention, the aforementioned transgenic mouse is characterized by having more than 8% or more than 10%~12% of chance to develop a lung tumor by the age of 1 or 2 months, or having more than 10% or more than 15%~20% of chance to develop a lung tumor by the age of 3 months, or having more than 20%, 25%, 30%, 35%, 40%, 45%, 50% or 55% of chance to develop a lung tumor by the age of 7 months.

Further in another embodiment of the invention, the aforementioned mouse is a transgenic FVB/N mouse.

Further in another embodiment of the invention, the aforementioned transgenic mouse has a lung tumor. The lung tumor is not associated with Clara cells. The transgenic mouse lung tumor stains negatively for Clara cell secretory protein (CCSP). The lung tumor shows no sign of metastasis in the mouse.

Further in another embodiment of the invention, the aforementioned transgenic mouse has a lung tumor that is associated with type II pneumocytes. The transgenic mouse lung tumor stains positively for prosurfactant protein C.

Further in another embodiment of the invention, the aforementioned transgenic mouse expresses Env protein in the lung tissues.

Yet in another embodiment of the invention, the lung tissue of the aforementioned transgenic mouse exhibits a higher level of phosphorylated p44/42 ERK than that of a non-transgenic control mouse.

In another aspect, the invention relates to a method for identifying a compound that affects tumorigenesis of human lung adenocarcinoma, comprising the steps of: (a) administering a test compound to a transgenic mouse, a lung tumor tissue and/or lung tumor cells isolated from the transgenic mouse, wherein the transgenic mouse has a genome that comprises a JSRV Env transgene operably linked to a surfactant protein C promoter (SPCp), and wherein the lung tissue of the mouse expresses the JSRV Env transgene, and further wherein the mouse is prone to developing a lung tumor; and (b) evaluating the effect of the test compound on the onset of lung tumor formation, lung tumor cell growth, and/or lung tumor size to determine whether the compound affects tumorigenesis of human lung adenocarcinoma.

In one embodiment of the invention, the aforementioned method in step (b) evaluates whether the test compound delays the onset and/or suppresses the growth of lung tumor in the mouse, lung tissue and/or lung tumor cells isolated therefrom.

In another embodiment of the invention, the aforementioned method in step (b) comprises the step of analyzing and assessing histopathological sections of a lung tumor obtained from the mouse.

Further in another aspect, the invention relates to a method for identifying a compound that affects tumorgenesis of human lung adenocarcinoma, comprising the steps of: (a) administering a test compound to a transgenic mouse, a lung tumor tissue and/or lung tumor cells isolated from the transgenic mouse, wherein the transgenic mouse has a genome that comprises a JSRV Env transgene operably linked to a surfactant protein C promoter (SPCp), and wherein the lung tissue of the mouse expresses the JSRV Env transgene and the mouse is prone to developing a lung tumor, and further wherein the mouse has a lung tumor; and (b) detecting the levels of p44/42 ERK and phospho p44/42 ERK proteins in the lung of the transgenic mouse, the lung tumor tissue and/or the lung tumor cells isolated therefrom to determine whether the test compound affects lung tumorigenesis of human lung adenocarcinoma. In this method, step (b) may comprise the step of detecting the levels of p44/42 ERK and phospho p44/42 ERK proteins by western blotting, and/or detecting the expression level of p44/42 ERK mRNA by quantitative reverse transcription polymer chain reaction (RT-PCR).

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 2A(b-d) are photographs showing lung tumors observed in Env transgenic mice at age of 4 months (b), 6 months (c), and 8 months (d).

FIG. 2B(b-e) are micrographs showing histochemically stained tissue sections with hemotoxylin and eosin to confirm the presence of malignant tumor cells in Env Transgenic line 1 (b, d) and Env Transgenic line 2 (c, e) mice. Magnification: 200× (b-c) and 400× (d, e).

[FIG. 4A: lane 6 and lane 10

DETAILED DESCRIPTION OF THE INVENTION

Definitions

Figure 1A:
FIG. 1A is a schematic representation of a JSRV envelope gene construct for creation of transgenic mice. The envelope gene from JSRV was cloned into the expression vector between lung-specific SPC promoter and SV40 poly A tail and used for embryo microinjections.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

SPC is an abbreviation for "surfactant protein C."

SPCp is an abbreviation for "surfactant protein C promoter."

SV40 is an abbreviation for "Simian virus 40."

As used herein, "cancer-prone" or "tumor-prone" shall generally means a high chance of developing a particular type of cancer or tumor when compared to a wild type animal.

As used herein, "tumor formation rate" or "chance of developing tumor" shall generally means the percentage of the animals that develop tumors.

As used herein, "tumor" shall generally means an abnormal growth of tissue resulting from uncontrolled, progressive multiplication of cells and serving no physiological function; a neoplasm. The term "tumor" encompasses "cancer" and "carcinoma."

As used herein, "carcinoma" shall generally mean a malignant and invasive epithelial tumor that spreads by metastasis and often recurs after excision; cancer.

As used herein, "is prone to developing a tumor" shall generally mean "having a natural inclination or tendency to develop a tumor in comparison with a non-transgenic control mouse.

As used herein, "tumorigenesis" shall generally means the process involved in the production of a new tumor or tumors, or formation or production of tumors.

As used herein, "mitogenic signal" shall generally means an agent that triggers mitosis. A mitogen is a chemical substance, usually some form of a protein, which encourages a cell to commence cell division, triggering mitosis. Mitogens trigger signal transduction pathways in which mitogen-activated protein kinase is involved, leading to mitosis. A mitogenic signal includes, but not limited to, PI-3K/Akt, Ras/Ref/MAPK and Stat3 pathways.

The present invention relates to a lung adenocarcinoma animal model. Lung tumors are induced in JSRV Env transgenic mice in immunocompetent FVB/N background. The invention also relates to the discovery of associated biochemical pathways, and establishment of stable lines of Env transgenic mice with targeted transformation of type II pneumocytes of lung and a high incidence of tumor formation. The transgenic mice disclosed here are useful as they can serve as an adequate model system for studying lung cancer and treatment.

The JSRV-SPC envelope transgenic immunocompetent mice develop spontaneous lung tumors as early as 1 month after birth. The lesion of adenocarcinoma exhibits highly similarity of pathology to human lung adenocarcinoma. The adenocarcinoma animal model of the invention provides a valuable tool for dissecting the pathways that mediate crucial aspects of cancer formation, metastasis and invasion. The non-human animal model of the invention also presents tremendous potential commercial applications in biopharmaceutical industry.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Cloning of JSRV Envelope Gene into an Expression Vector

To determine whether an animal model for spontaneous pulmonary adenocarcinoma could be successfully and robustly established in transgenic mice, the SPCp-JSRV Env transgene vector was constructed and transgenic mice were produced. Jaagsiekte sheep retrovirus (JSRV) envelope gene (Genbank Accession No. AF105220; SEQ ID NO:5) (gifted from Hung Fan, University of California, Irvine, USA) was amplified by PCR and inserted into the SPC/SV40 vector at the multiple cloning sites using SalI and HindIII to obtain SPC-Env construct. The primers used to amplify the 1845 by envelope gene were 5'-TTCCCATGGATGCCGAAGCGC-CGCGCT-3' (SEQ ID NO: 1) as a forward primer and 5'-CT-TAAGCTTTCACGGGTCGTCCCCCGCATC-3' (SEQ ID NO: 2) as a reverse primer. The conditions of PCR were the following: initial denaturation for 5 min at 94° C., 30 PCR cycles were performed for 45 sec at 94° C., 45 sec at 60° C., for 90 sec at 72° C., followed by a final 7 min extension at 72° C. The encoding sequence in the SPC-Env plasmid has been confirmed by DNA sequencing.

Creation and Maintenance of JSRV Env-Transgenic Mice

JSRV Env-transgenic animals were generated by microinjection of 1.0 ng of linear SPC-Env construct into fertilized FVB/N mouse embryos at single cell stage, which were subsequently implanted into pseudo pregnant FVB/N female mice, generating transgenic animals following the protocol described previously (Brinster et al., (1985) "Factors affecting the efficiency of introducing foreign DNA into mice by microinjecting eggs" *Proc Natl Acad Sci USA* 82(13), 4438-42). FVB/N mice were purchased from National Applied Research Laboratories-Laboratory Animal Center, Taiwan. SPC-Env plasmids were linearized with the restriction enzyme HindIII and recovered from agarose gels (Thermo Fisher Scientific, IL, USA) with a gel extraction kit (Qiagen, Germany). Transgenic lineages were maintained by crossmating of Env-transgenic individuals to obtain Env-transgenic FVB/N F1 inbred mice. Mice were maintained in accordance with institutional animal use protocol.

Genotyping and the Detection of Envelope Gene Expression

Genomic DNA was extracted from transgenic mice tails with Tissue & Cell genomic DNA purification kit (GeneMark, Taiwan ROC). Env transgene was detected in genomic DNA by PCR to amplify a 474 bp region (252-725 bp) using the following primers: forward: 5'-GCG TACAT-TCCTGATCCGCCAATG-3' (SEQ ID NO: 3) and reverse: 5'-CGGATGCTGT CCTCGATATTCAGG-3' (SEQ ID NO: 4), which would recognize the surface domain (SU) coding sequence of the JSRV envelope gene. The PCR conditions were as follows: initial denaturation for 5 min at 94° C., 30 PCR cycles were performed for 45 sec at 94° C., 45 sec at 55° C. and 45 sec at 72° C., followed by a final 7 min extension at 72° C. The amplicon size was 473 bp.

The expression of the transgene JSRV envelope was detected by reverse transcription polymerase chain reaction (RT-PCR) analysis. Total RNA was isolated from Env transgenic mice lungs with tumors as well as from normal mice. RNA was isolated from mice's lungs using TRIZOL reagent (Invitrogen, CA, USA) following the manufacturer's instructions. Purity of the isolated RNA was evaluated spectrophotometrically by the A260/A280 absorbance ratio. Two micrograms of total RNA were used for reverse transcription polymerase chain reaction (RT-PCR) to amplify the mRNA of Env gene using one-step RT-PCR Premix reagent (iNtRON Biotechnology, Korea). The primers used were the same as in genomic PCR reaction, with the same amplicon size. The RT-PCR reaction condition was as follows: reverse transcription for 30 min at 45° C., initial denaturation for 5 min at 94° C., 35 PCR cycles were performed for 1 min at 94° C., 1 min at 55° C., 1 min at 72° C., followed by a final 7 min extension at 72° C.

Quantification of Env Gene Expression

The expression levels of Env mRNA in the lung tumors from transgenic mice were assessed by quantitative PCR analysis (The LightCycler® 480 Real-Time PCR system) using Env gene specific primer pairs, the forward primer 5'-CGAGTGACTATCTCAGGCATTG-3' (481-502 bp; SEQ ID NO: 5) and the reverse primer 5'-TAGTATGCCCTTGC-CTAGAC-3' (522-541 bp; SEQ ID NO: 6), and the probe set No. 48, ACTGGGAA (Cat. No. 04688082001; SEQ ID NO: 7), from the Roche Universal Probe Library Assay Design Center (Roche, Switzerland). The plasmid carrying Env gene at different concentrations (5, 0.5 and 0.05 pg/ml) was used as a standard. The number of cycles needed for amplification of Env gene from the two lineages of transgenic mice was compared. Statistical analysis was performed using unpaired Student's t test.

Histochemisry and Immunostaining

Whole lungs were excised from the mice and fixed in 10% formalin (Sigma-Aldrich, USA) solution overnight and embedded in paraffin (Thermo Fisher Scientific, IL, USA) for sectioning. The sections were processed and stained with 1% hematoxylin and eosin solution (Sigma-Aldrich, USA). For immunohistochemistry, the sections were stained with rabbit polyclonal anti-Clara cell secretory protein (CCSP) antibody (1:200 dilution, Millipore, CA, USA) or rabbit polyclonal anti-prosurfactant protein C antibody (1:400 dilution, Millipore, CA, USA) or mouse monoclonal anti-Env antibody (1:50 dilution, a gift from Dr. Dusty Miller, University of Washington, USA) followed by appropriate secondary antibodies. Bright field microscopy pictures were taken at 200× and 400× magnifications.

Western Blot Analysis.

Tumor-bearing lung tissues from 7-month-old mice were cut to pieces and ground in an ice-cold lysis buffer (50 mM Tris-HCl, 150 mM NaCl, 1% Triton X-100 and 1X protease inhibitor cocktail (Roche, Switzerland)) to prepare cell lysate. Cell debris was removed by centrifugation at 14,000×g for 20 minutes at 4° C. The proteins were separated by SDS-PAGE and transferred onto Hybond ECL nitrocellulose membrane (GE healthcare, UK) and probed with polyclonal antisera raised against p44/42 MAPK, phospho p44/42 MAPK Thr202/Tyr204, Akt, phospho Akt Ser473, phospho Akt Thr308 (Cell Signaling Technology, USA) followed by anti-rabbit and anti-mouse secondary antibodies conjugated to HRP (Thermo Fisher Scientific, IL, USA) and detected by ECL using SuperSignal West Pico chemiluminescent substrate (Thermo Fisher Scientific, IL, USA).

Results

Generation and Screening of JSRV Envelope Transgenic Mice

Figure 1B:
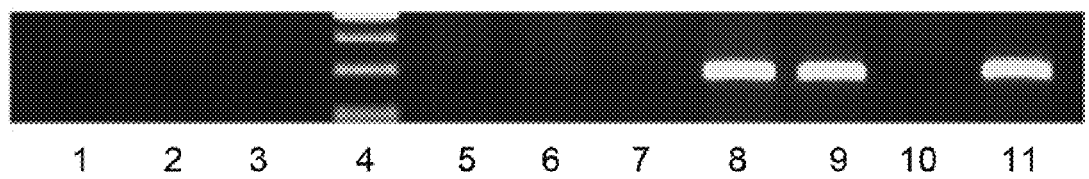
FIG. 1B is a photograph of gel electrophoresis analysis of PCR products of tail DNA of Env transgenic FVB/N F0 mice using a primer pair that would recognize the transgene JSRV Env inserted into the genomic DNA of the mice to screen for the presence of Env transgene. Lanes 1-3: FVB/N mice, lanes 5-11: FVB/N F0 mice, lane 4: 1 kb ladder. The amplicon size was 474 bp.

The transducing vector SPC/SV40 has been used in transgenic mouse models to achieve high levels of transgene expression restricted to pulmonary epithelial cells. The surfactant protein C (SPC) promoter has been characterized to have a unique lung tropism and is activated only in lung alveolar epithelium. It has been used to drive lung-specific transgene expression in many transgenic animal models including SV40 large T antigen, RON receptor tyrosine kinase transgenic mice and Notch3 transgenic mice. In order to study JSRV Env-mediated tumorigenesis in mice lungs, a full-length Env cDNA from JSRV was cloned into SPC/SV40 vector between lung-specific SPC promoter and SV40 polyA tail to create SPC-JSRV Env construct (FIG. 1A). FVB/N mice embryos were microinjected with this construct to generate Env transgenic mice. The founders were then cross-mated with wild-type FVB/N mice to produce F1 progenies. Preliminary screening of F1 transgenic mice was carried out by performing genomic PCR on tail DNA using primers specific to the surface domain of the envelope gene to amplify a 474 bp (252-725 bp) region. Three mice that carried the Env transgene were identified by genomic PCR—No. 8 (male, m), No. 9 (female, f) and No. 11 (f) that carried the Env transgene (FIG. 1B). The F1 transgenic mice were cross-mated to produce two lineages of F2—No. 8 x No. 9 (Env Tg line 1) and No. 8 x No. 11 (Env Tg line 2). See Ebenezer Chitra, Shu-Ling Yu, Kuang-Nan Hsiao, Hsiao-Yun Shao, Charles Sia, I-Hua Chen, Shih-Yang Hsieh, Jen-Hao Chen, Yen-Hung Chow (2009) "Generation and characterization of JSRV envelope transgenic mice in FVB background" Virology 393: 120-126, which is incorporated herein by reference in its entirety.

Incidence of Lung Tumors in Env Transgenic Mice

Figure 2A:
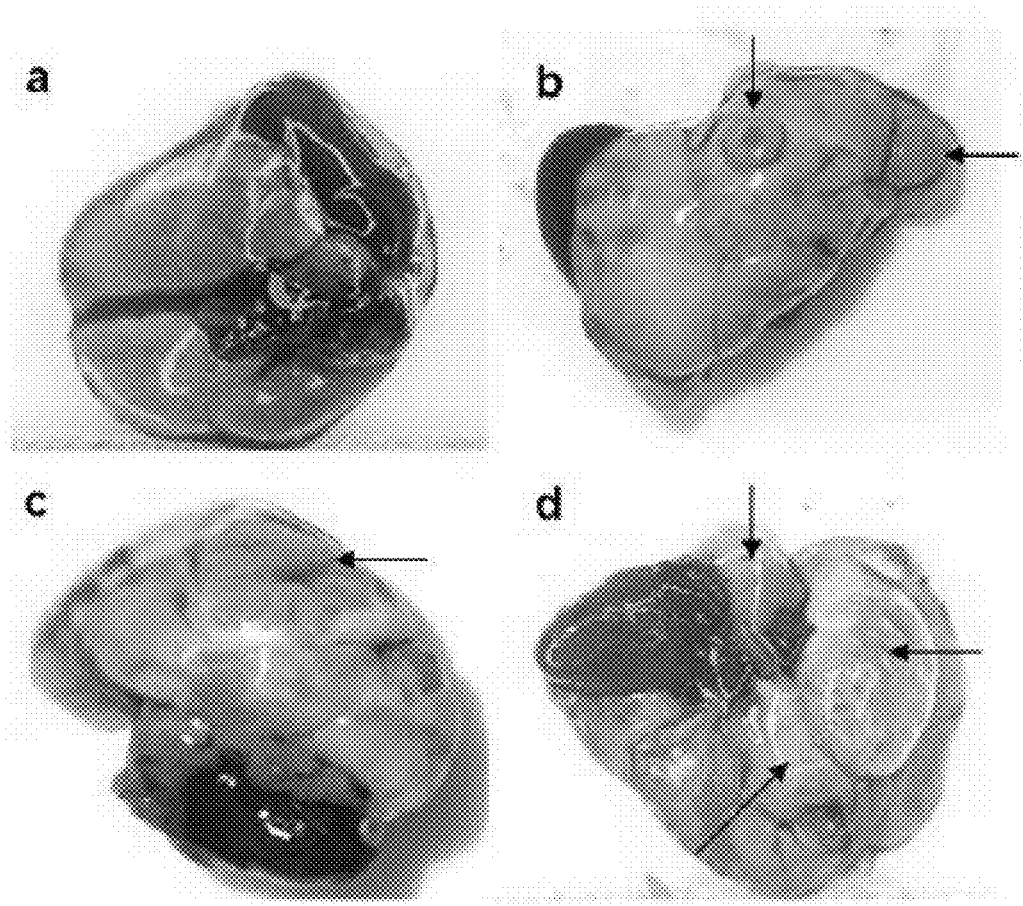
FIG. 2A(a) is a photograph showing a normal lung from an FVB/N mouse.
Figure 2B:
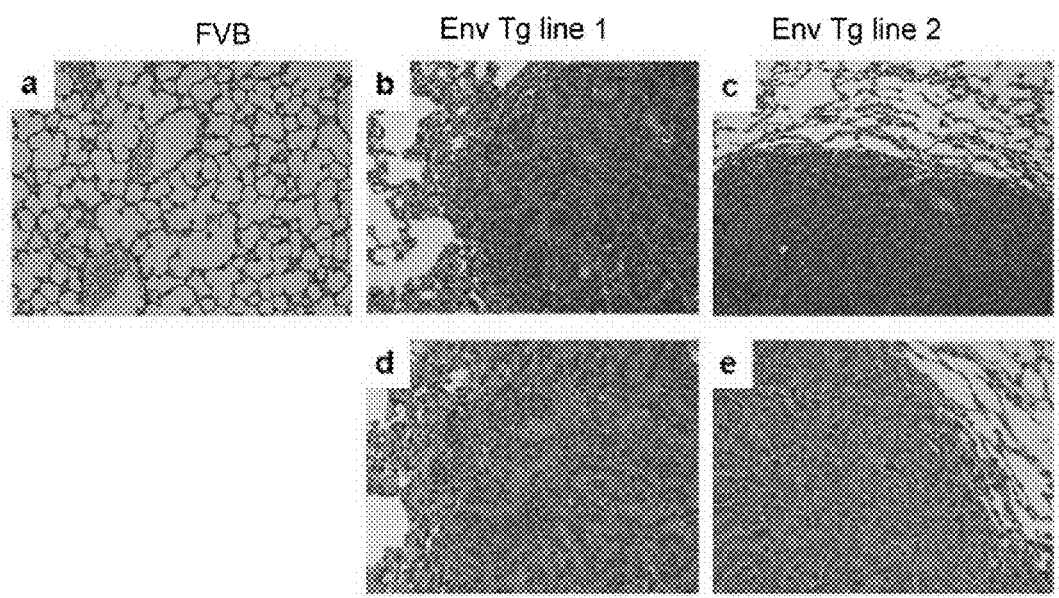
FIG. 2B(a) is a micrograph showing a histochemically stained lung tissue section of a normal FVB/N mouse lung with hemotoxylin and eosin. Magnification: 200×.

The two F2 transgenic lines were bred and maintained. Mice were sacrificed at periodic intervals and monitored for tumor formation. Visible multifocal tumors, similar to those found in OPA of JSRV-infected lambs, could be seen in the periphery of the lungs of F2 transgenic mice from 1 month onwards with an increase in the tumor size with age while no tumor developed in the FVB/N mice. The tumors observed in 4-month-old mice were about 0.1-0.2 cm in diameter, at 6 months they were 0.2-0.4 cm and at 8 months they were more than 0.5 cm in diameter (FIG. 2A). The potency of developing larger tumors was more in Env Transgenic line 2 mice than in Env Transgenic line 1 in the similar age group. A comparison of the frequency of tumor formation in the two lines of transgenic mice showed that Env Transgenic line 2 mice had an increased tumor incidence rate compared to Env Transgenic line 1 mice at each time point of examination. The frequency of tumor formation at 6-7 months of age was about 56% in Env Transgenic line 1 (9/16), and 71% in Env Transgenic line 2 (10/14) (Table 1). Based on the above observations, Env Transgenic line 1 was found to be less tumorigenic than Env Transgenic line 2. In both transgenic lines no malignancy was observed in other organs or tissues such as liver, spleen, intestines or thoracic muscle over a one year follow-up period. Tumor-bearing lungs from both Env Transgenic lines were stained histochemically with hemotoxylin and eosin to confirm the presence of malignant tumor cells. While lungs from the FVB mice showed regular histology, the transgenic mice lungs showed distinct development of adenocarcinoma (FIG. 2B). The tumor was composed of neoplastic cells having multiple hyperchromatic nucleoli and eosinophilic cytoplasm. It appeared to be surrounded by areas of alveoli, which suggests it to be a peripheral lung tumor involving distal alveoli.

TABLE 1

|  | Age (months) | No. of mice with lung tumors | Tumor incidence rate (%) | Tumor in other organs |
|---|---|---|---|---|
| Env Tg line 1 | I | 1/6 | 16.7 | 0/6 |
|  | II | 1/6 | 16.7 | 0/6 |
|  | III | 2/8 | 25 | 0/8 |
|  | V | 1/8 | 12.5 | 0/8 |
|  | VII | 9/16 | 56.3 | 0/16 |
| Env Tg line 2 | I | 5/9 | 55.3 | 0/9 |
|  | II | 2/6 | 33.3 | 0/6 |
|  | III | 4/8 | 50 | 0/8 |
|  | V | 4/11 | 36.4 | 0/11 |
|  | VI | 10/14 | 71.4 | 0/14 |

Tumors Formed by Type II Pneumocytes of Lungs

Figure 3A:
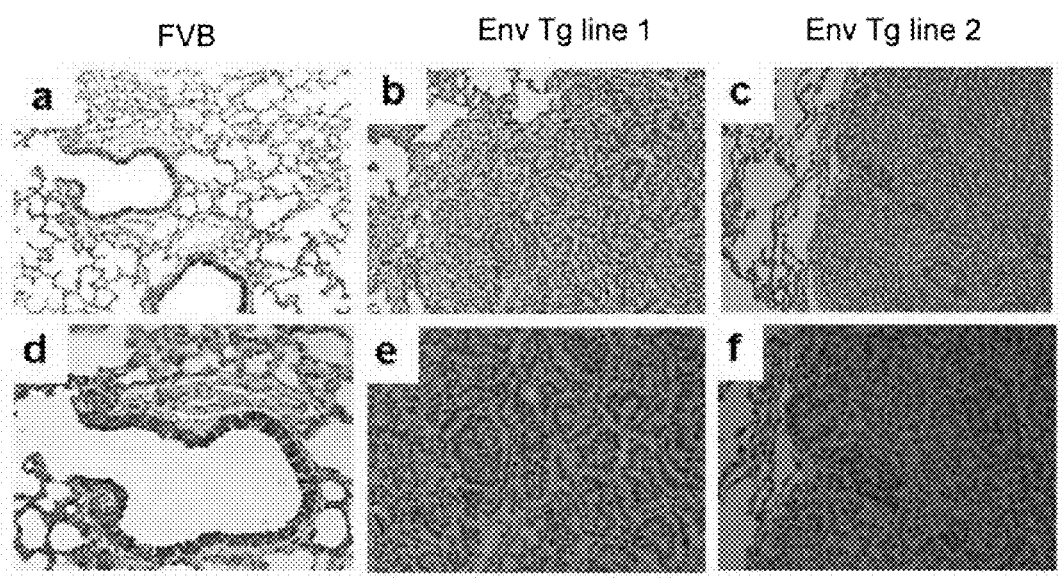
FIGS. 3A(a-f) are micrographs showing the results of immunohistochemical analysis of lung sections with anti-Clara cell secretory protein antibody specific for Clara cells in FVB/N (a, d), Env Transgenic line 1 (b, e) and Env Transgenic line 2 (c, f) mice. Magnification: 200× for top panel (a-c) and 400× for bottom panels (d-f).
Figure 3B:
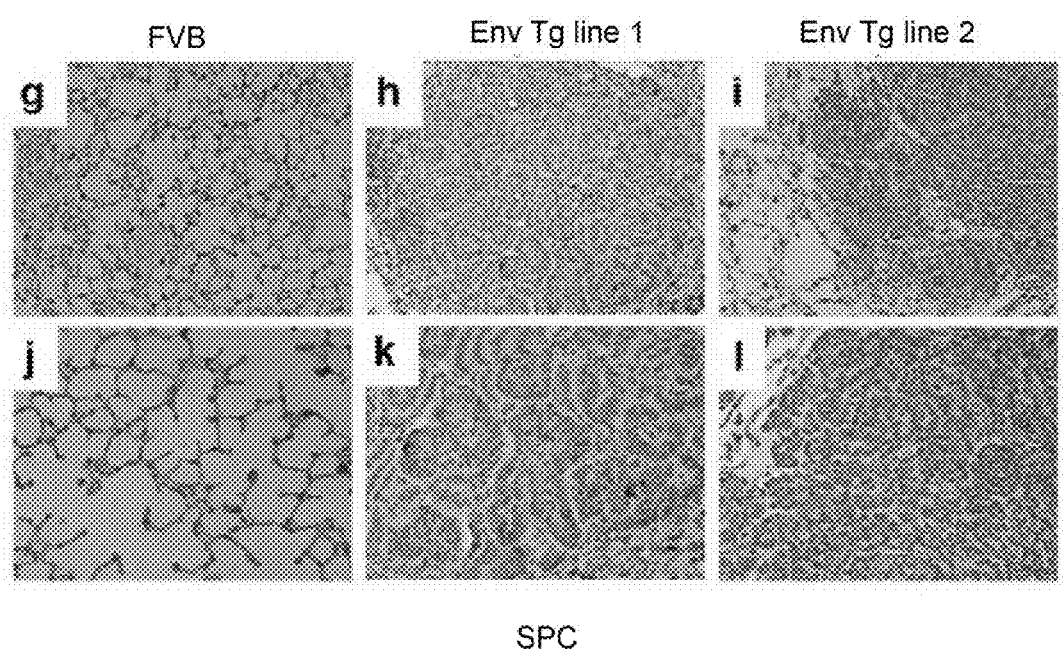
FIGS. 3B(g-l) are micrographs showing anti-proSPC antibody specific for type II pneumocytes in FVB/N (g, j), Env Transgenic line 1 (h, k) and Env Transgenic line 2 (i, l) mice. Magnification: 200× for top panel (g-i) and 400× for bottom panels (j-l).
Figure 3C:
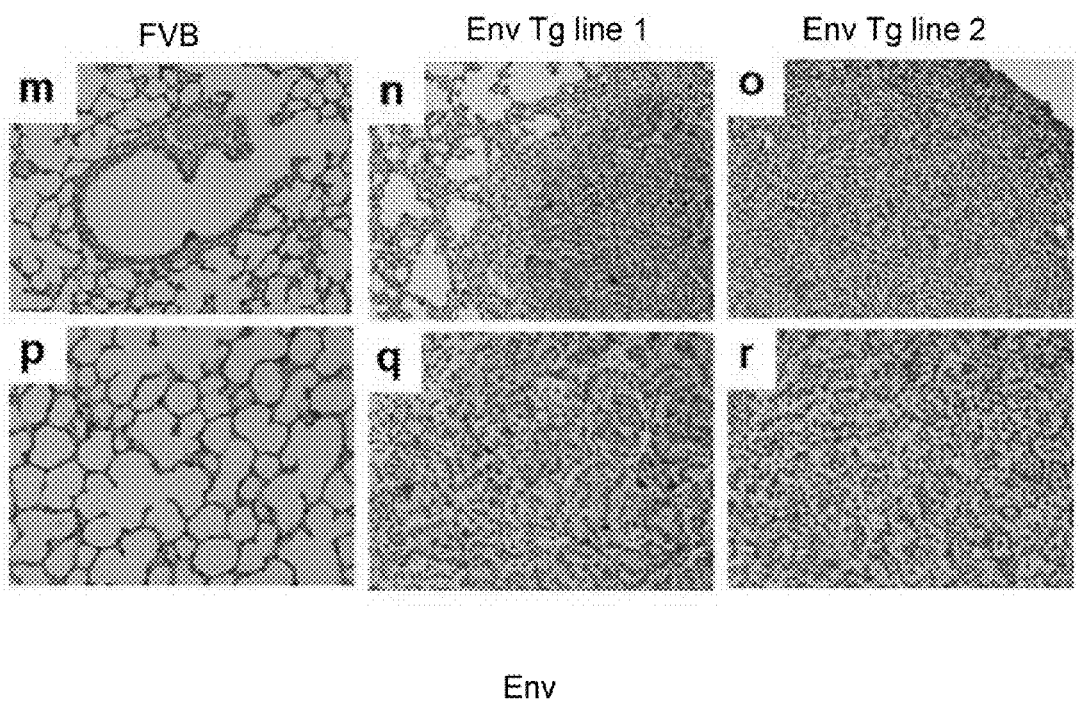
FIGS. 3C(m-r) are micrographs showing anti-Env antibody specific for JSRV envelope protein in FVB/N (m, p), Env Transgenic line 1 (n, q) and Env Transgenic line 2 (o, r) mice. Magnification: 200× for top panel (m-o) and 400× for bottom panels (p-r).

JSRV Env gene is sufficient to induce lung tumors when expressed in the lungs of newborn lambs. Both naturally occurring and experimentally induced OPA have been shown to involve predominantly alveolar type II pneumocytes and Clara cells. To corroborate these observations, we examined the tissue type of malignant cells in the transgenic mice by immunohistochemical (IHC) staining using antibody specific to Clara cell secretory protein (CCSP, a marker of Clara cells) (FIG. 3A) and antibody specific to proSPC (a marker of type II pneumocytes) (FIG. 3B). FIGS. 3A-3C show the results of tissue typing of tumor cells in the lung of transgenic mice by immunohistochemistry. In the normal FVB/N mouse lung, immunostaining for CCSP was observed in the bronchial lining, showing normal distribution of Clara cells (panels a, d). Tumor lesions from 4-month-old mice of Env transgenic line 1 and Env transgenic line 2 showed no positivity for the CCSP marker (panels b, e and c, f respectively) suggesting that the tumor was not constituted of Clara cells. In normal FVB/N lung, type II pneumocytes showed a dispersed distribution (panels g, j). The tumor cells from both transgenic lines showed positive cytoplasmic staining for proSPC (panels h, k and i, l), suggesting that the tumor was composed of type II pneumocytes. In essence, lung tumor developed in the Env transgenic mice expressed proSPC but not CCSP, implying that Env-mediated transformation indeed targeted type II pneumocytes of the lungs leading to development of lung tumors.

Expression Level of Env in Transgenic Mice

In order to confirm the expression of JSRV Env in the lungs of transgenic mice, RT-PCR and IHC were performed. Tissue sections were stained with anti-JSRV Env monoclonal antibody (B3+C9, gifted by Dr. Miller) (FIG. 3C). While the normal mouse lung had no expression of Env protein (panels m, p), lung tumors from both transgenic lines showed distinct cytoplasmic staining for Env (panels n, q and o, r), thereby confirming transgene expression. The Env expression was also detected in the non-tumor portion of the transgenic mice lungs.

Figure 4A:
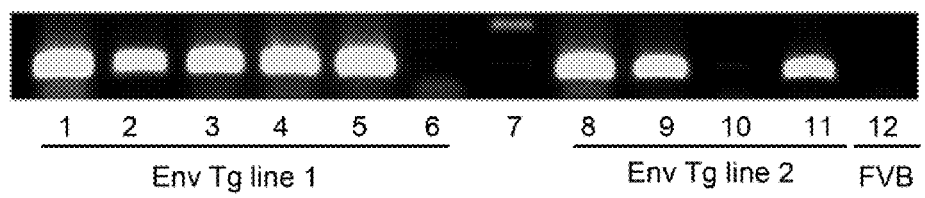
FIG. 4A shows the results of RT-PCR analysis of RNA extracted from the lung tissues of Env transgenic and normal FVB/N mice to analyze the expression of Env transgene in the transgenic mice. Results are shown for Env Transgenic line 1 (lanes 1-6), Env Transgenic line 2 mice (lanes 8-11), FVB/N mice (lane 12) and 1 kb ladder (lane 7). Amplicon size: 474 bp.

Total RNA was extracted from the lung tissue of 4-month-old mice and analyzed by RT-PCR using Env-specific primers to confirm Env gene expression. A PCR product corresponding to 474 bp was obtained from both Env Transgenic line 1 (No. 1-6) and Env Transgenic line 2 (No. 8-11) mice confirming the expression of Env transgene (FIG. 4A).

Figure 4B:
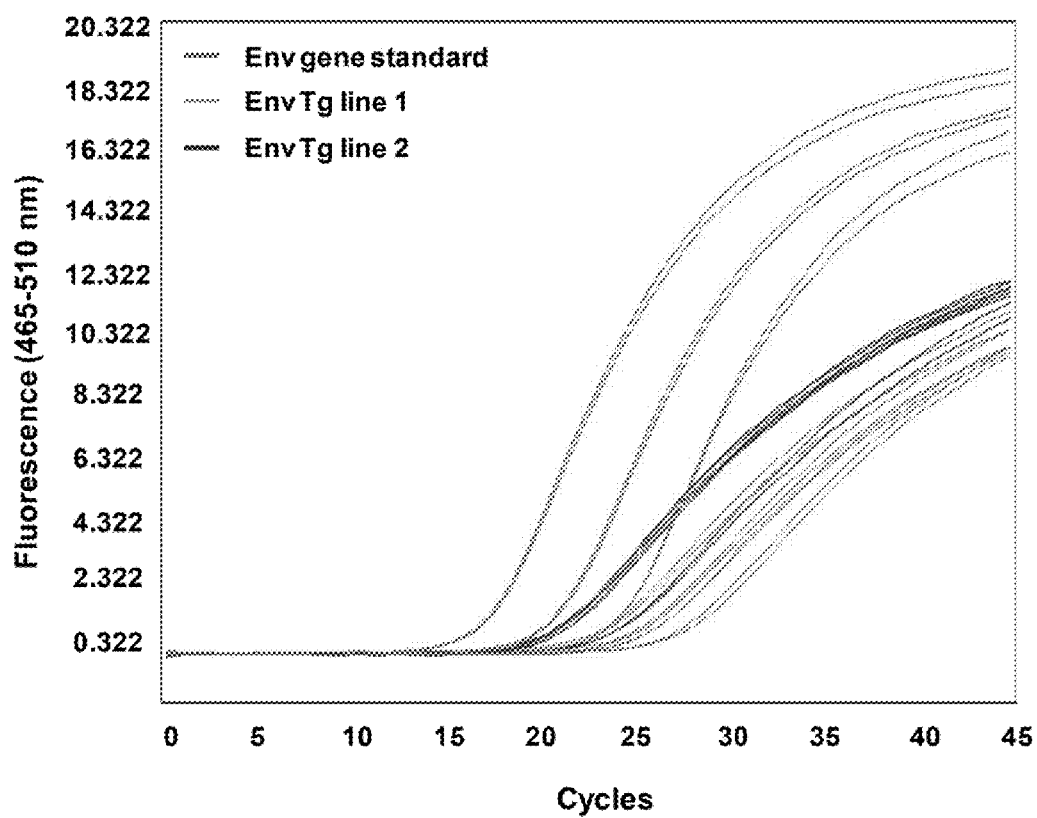
FIG. 4B shows a quantitative RT-PCR analysis of RNA extracted from transgenic mice lungs to quantify Env gene expression levels in Env Transgenic line 1 and Env Transgenic line 2 mice compared to Env gene carrying plasmid DNA as standard. The average numbers of PCR cycles needed for fluorescent detection of Env gene expression are represented in FIG. 4C.
Figure 4C:
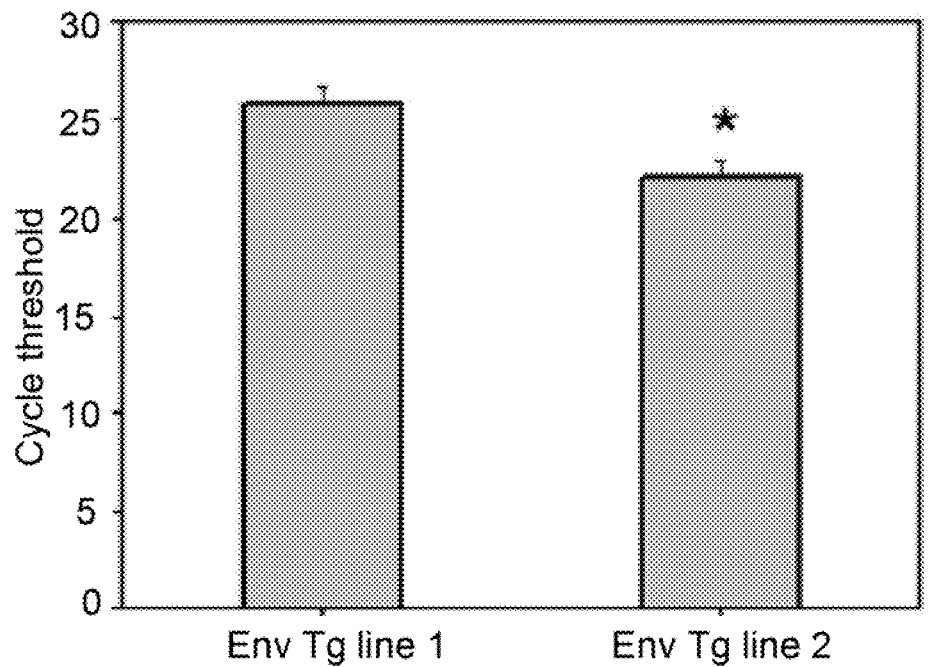
FIG. 4C is a graph showing the average PCR cycle threshold for detection of Env gene by quantitative RT-PCR from Env Transgenic line 1 and line 2 mice lungs. (*P=0.019)

Since Env Transgenic line 2 mice showed more malignancy in terms of tumor incidence (Table 1) as well as tumor size, we measured the Env gene expression levels in both groups by quantitative RT-PCR using primers to amplify a 61 bp region of Env gene. Env Transgenic line 2 was found to have an increased level of expression of Env gene with detectable signal observed after 22 cycles of PCR (blue line) while Env Transgenic line 1, on the other hand, gave detectable signals only after 26 PCR cycles (FIGS. 4B and 4C). The approximate difference in cycling threshold ($\Delta C_t$) would be at least 2, and therefore at least a four-fold increase in Env gene expression was evident in Env Transgenic line 2 compared to Env Transgenic line 1. Our results indicate that the increased expression of Env could account for the increased malignancy observed in Env Transgenic line 2.

Induction of MAPK and PI3K Pathways in Env Transgenic Mice

Figure 5:
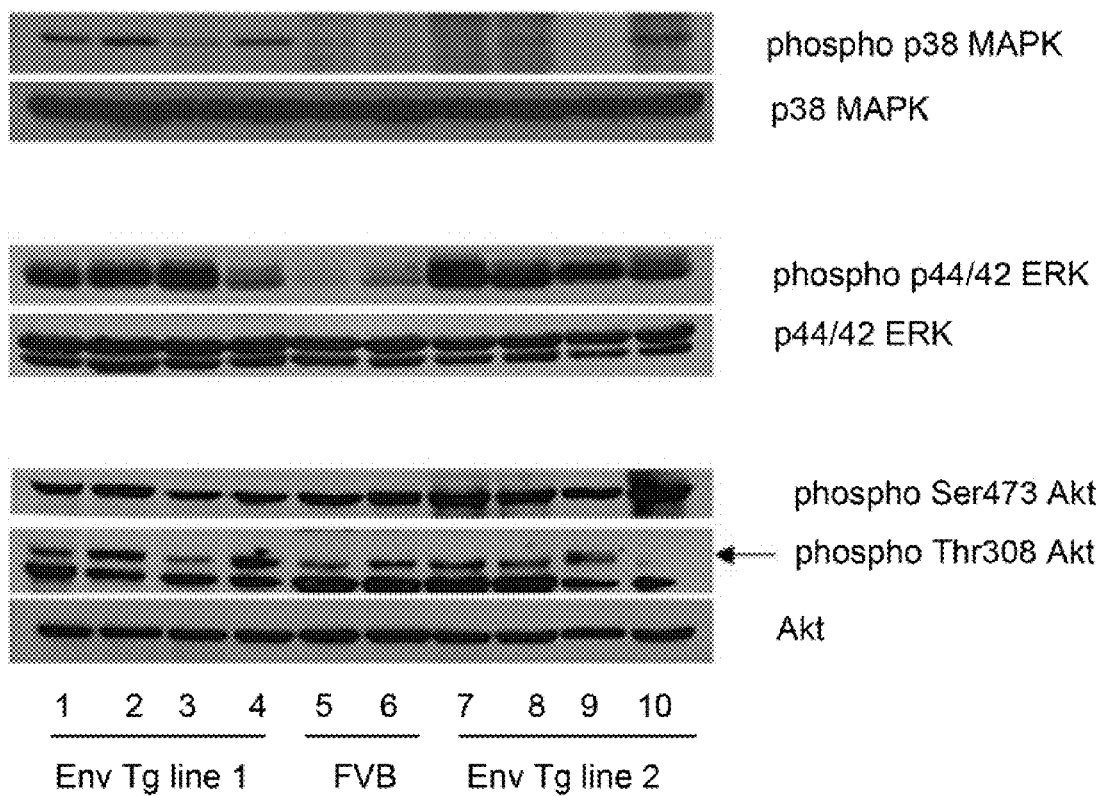
FIG. 5 is a photograph showing a Western blot analysis to detect signaling pathways induced in transgenic mice. Lysates were prepared by homogenization of lung tissues excised from the two lines of transgenic mice and normal FVB/N mice. The results show the levels of phospho p44/42 ERK, p44/42 ERK, phospho p38 MAPK, p38 MAPK, phospho Ser473 Akt, phospho Thr308 Akt and Akt in Env Transgenic line 1 (lanes 1-4), Env Transgenic line 2 (lanes 7-10) mice and FVB/N (lanes 5,6) mice.

MAPK and PI3K pathways have been indicated in Env-mediated transformation of target cells in vitro as well as in viva. This prompted us to analyze the activation status of signaling pathways in the lungs of transgenic mice. Cell lysates were prepared from the tumor-bearing lungs from Env Transgenic line 1 and Env Transgenic line 2 mice and the phosphorylation pattern of the major signaling proteins, p38 MAPK, p44/42 ERK and Akt were analyzed. It was observed in the immunoblot analyses that p44/42 ERK was strongly phosphorylated in all the Env transgenic mice compared to normal FVB/N mice. Phosphorylation of p38 MAPK was induced in 3 mice from Env Transgenic line 1 and one mouse from Env Transgenic line 2 compared to FVB/N control mice. Analysis of phosphorylation status of Akt at Ser473 and Thr308, the residues involved in Akt activation revealed that while there was no change in phosphorylation at Thr308 of Akt, only two mice showed increased phosphorylation at Ser473 in the transgenic mice compared to normal mice (FIG. 5). This suggests that Akt pathway is not specifically activated above normal levels by Env transgene expression in the lungs. These data indicate that in our transgenic mice ERK pathway seems to play a significant role in tumorigenesis.

Discussion

The present study describes the creation and characterization of JSRV Env transgenic mice in immunocompetent FVB/N background under the lung-specific SPC promoter. We have observed spontaneous induction of lung tumors from one month of age onwards in our transgenic mice, with a progressive increase in tumor incidence and tumor size with age. We have confirmed Env gene expression in the lungs by RT-PCR and by immunohistochemistry using anti-Env monoclonal antibody. Tumor formation was monitored for over one year in the transgenic animals. A variable extent of metastasis of JSRV-induced lung tumors in sheep has been reported, but we did not observe any metastasis in our transgenic mice (Table 1).

We obtained two lines of Env transgenic mice with different levels of Env gene expression as determined by quantitative RT-PCR (FIG. 4). Higher tumor incidence rate observed in Env Transgenic line 2 could be correlated to higher expression levels of the Env transgene as compared to Env Transgenic line 1. It is a notable finding that expression levels of Env play a role in the extent of cellular transformation and malignancy induced in transgenic animals.

The expression of Env was found to be restricted to type II pneumocytes of lung tissue (proSPC+ve, Env+ve and CCSP−ve), attributed to the use of the SPC promoter specific for this cell type. The surfactant protein C is a component of pulmonary surfactant of the lung; it is active in type II pneumocytes and is expressed in 80% of the tumor cells of JSRV-induced OPA (Platt et al., (2002) "Alveolar type II cells expressing jaagsiekte sheep retrovirus capsid protein and surfactant proteins are the predominant neoplastic cell type in ovine pulmonary adenocarcinoma" *Vet Pathol* 39(3), 341-52). Tumor cells of both OPA and human lung adenocarcinoma express markers of type II pneumocytes and Clara cells. JSRV is unique among retroviruses in being able to transform these cell types. The long terminal repeats (LTR) promoter and enhancer of JSRV exhibit transcriptional specificity for secretory lung epithelial cells.

Previously, lung tumors primarily composed of type II pneumocytes were induced in immunodeficient mice by expressing Env gene using adeno-associated virus (AAV) vector (Wootton et al., ibid.), but ultimately the mice succumbed owing to lethality. Yet, expression of Env gene in immunocompetent mice using AAV was not successful and tumor development was blocked.

Recently, immunocompetent Env transgenic mice expressing Env gene under the surfactant protein A (SPA) promoter were created but they developed only subdermal lipomas with a low tumor incidence rate and low efficiency of transgene expression in the lung (Dakessian et al., ibid.). Though they had initially selected the SPC promoter for creation of Env transgenic mice, after failed transplants of microinjected embryos, they switched to using the SPA promoter to express Env gene with HA tag. They claim that HA tag reduced the transforming potency of Env, which might explain the low tumor incidence rate. They conclude that since the SPA promoter responds to the transcription factor C/EBP$_\alpha$ that was found in abundance in adipocytes and lung epithelial cells, this might have induced the lipomas.

While we did not observe any lethality using the SPC promoter, we could achieve specific expression of Env in type II pneumocytes of our transgenic mice lungs resulting in spontaneous induction of multifocal lung tumors from the age of one month onwards. Dakessian and coworkers (Dakessian et al., ibid.) used a mixed background of mice parentage (Balb/c X C57/B16J) for injection of the transgene and crossed it with FVB/N mice to generate F1s. We have used FVB/N mice for introduction of transgene; these mice are known to have higher tumor incidence rates and are ideal for microinjection and creation of transgenic mice. Our successful creation of JSRV Env transgenic mice might be attributed to the choice of the promoter, mouse background and use of Env gene per se without any tag, which has enabled us to breed and maintain these animals for over 1 year. Another notable contribution of our model is that we created two transgenic lines with variable levels of Env expression allowing us to assess Env dose-dependent effect on tumorigenesis.

It has been reported that immunohistochemical staining of tumor tissues from experimental and natural OPA showed strong activation of Raf, MEK and ERK, and that pharmacological inhibitors for Ras and MEK completely inhibited transformation of NIH 3T3 fibroblasts in vitro, confirming the major role of MEK-ERK signaling pathway in Env-induced transformation of target cells. It, however, has been shown that Akt phosphorylation was not observed by immunohistochemical staining of lung tumor sections of naturally occurring OPA in sheep and that PI3K was not required for JSRV envelope-induced transformation of mouse fibroblast cells in vitro (Maeda et al., (2003) "Transformation of mouse fibroblasts by Jaagsiekte sheep retrovirus envelope does not require phosphatidylinositol 3-kinase" *J Virol* 77(18), 9951-9). Corroborating these findings, our transgenic mice also show a strong induction of ERK phosphorylation without any significant change in phosphorylation status of Akt. It has been reported that MAPK (p38) is constitutively activated in transformed cells in vitro, but that in vivo not all tumors showed activation of p38 MAPK (Maeda et al., (2005) "Roles of the Ras-MEK-mitogen-activated protein kinase and phosphatidylinositol 3-kinase-Akt-mTOR pathways in Jaagsiekte sheep retrovirus-induced transformation of rodent fibroblast and epithelial cell lines" *J Virol* 79(7), 4440-50), which is similar to what we have observed in our transgenic mice. Our observations indicate a greater role for p44/42 ERK pathway in Env-mediated tumor formation in vivo.

The generation of transgenic mice carrying Env oncogene is valuable in determining the effects of this gene upon tumor development and oncogenesis. The results indicate that JSRV Env gene under the control of SPC promoter achieves targeted transformation of type II pneumocytes, leading to induction of lung tumors in our transgenic mice. It has been reported that OPA caused by natural infection of JSRV and human lung adenocarcinoma share many similarities in clinical and histological features and therefore transgenic mice with Env-induced lung tumors have the potential to serve as animal models for human lung cancer. This mouse model can be used to study the molecular mechanisms of oncogenic transformation, for assessing the potential carcinogenic risk of environmental agents and for screening anti-cancer agents.

In summary, the JSRV Env transgenic mice of the invention developed spontaneous lung adenocarcinoma. The characteristics of the transgenic mice of the invention, however, clearly distinguish from the transgenic mice generated by Dakessian et al. (ibid.) in many aspects, such as the introduced transgene construct, the mouse genetic background, the expression level of the transgene, the onset and incidence of tumor formation, the stability and easiness of maintenance of the transgenic lines, etc. The transgenic mice reported by Dakessian contains a transgene composed of JSRV Env plus 5' untranslated long terminal repeats (LTR) region under the control of surfactant protein A promoter. The transgene could be silent due to inactivator binding to LTR. Their mice developed lung tropism tumor with an onset of about 225 days (7.5 months) and a tumor formation rate of 9.1% (2/22). Their transgenic lineages were unstable.

By contrast, the JSRV Env transgenic mouse of the invention contains a transgene composed of JSRV Env plus an SV40 poly A tail under the control of surfactant protein C promoter. The transgene is highly expressed. The mice developed lung tropism tumor as early as one month, had a high incidence of tumors with a tumor formation rate of 83.3% (10 out of 12 mice 8 months old developed lung tumors). The transgenic lines are stable for over one year and easy to maintain and breeding, and suitable for many applications, such as drug screening for anti-cancer therapeutic agents and studies of mechanisms of tumorigenesis (Xiong et al., (2003) "Expression of hepatitis B virus X protein in transgenic mice." *World J Gastroenterol* 9(1):112-6; Lee et al., (2009) "Profiling of transcripts and proteins modulated by K-ras oncogene in the lung tissues of K-ras transgenic mice by omics approaches." *Int J Oncol* 34(1):161-72; Chesler et al., (2008) "Chemotherapy-induced apoptosis in a transgenic model of neuroblastoma proceeds through p53 induction." *Neoplasia* 10 (11):1268-74).

The JSRV Env-transgenic mouse model of the invention is a valuable tool for investigation of mitogenic signals. Env transformation of target cells has been reported to involve PI3K/Akt pathway in rodent (e.g., NIH 3T3 and 208F cells), chicken (CEF and DF-1), and MDCK dog epithelial cells as well as MAPK signaling pathway in NIH3T3 mouse fibroblasts and RK3E rat epithelial cells. Mitogenic signals such as PI-3K/Akt, Ras/Ref/MAPK and Stat3 pathways may be examined in the mouse model of the invention.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A transgenic mouse whose genome comprises a Jaagsiekte sheep retrovirus (JSRV) envelope protein (Env)-encoding transgene operably linked to a surfactant protein C promoter (SPCp), wherein the lung tissue of the transgenic mouse expresses the transgene, and wherein the transgenic mouse is characterized by having more than 5% of chance to develop a lung tumor by the age of 1 month, or having more than 8% of chance to develop a lung tumor by the age of 3 months, or having more than 20% of chance to develop a lung tumor by the age of 7 months, and further wherein the transgenic mouse has an FVB/N genetic background.

2. The mouse of claim 1, wherein the mouse is characterized by having more than 10%~12% of chance to develop a lung tumor by the age of 1 or 2 months, or having more than 10% or more than 15%~20% of chance to develop a lung tumor by the age of 3 months, or having more than 25% of chance to develop a lung tumor by the age of 7 months.

3. The mouse of claim 1, wherein the mouse is characterized by having more than 8% of chance to develop a lung tumor by the age of 1 month, or having more than 15%~20% of chance to develop a lung tumor by the age of 3 months, or having more than 30% of chance to develop a lung tumor by the age of 7 months.

4. The mouse of claim 1, wherein the transgenic mouse is characterized by having more than 35%, 40%, 45%, 50% or 55% of chance to develop a lung tumor by the age of 7 month.

5. The mouse of claim 1, wherein the mouse has a lung tumor.

6. The mouse of claim 5, wherein the lung tumor shows no sign of metastasis in the mouse.

7. The mouse of claim 5, wherein the mouse lung tumor stains negatively for Clara cell secretory protein (CCSP).

8. The mouse of claim 5, wherein the mouse lung tumor stains positively for prosurfactant protein C.

9. The mouse of claim 1, wherein the transgene has no HA tag.

10. The mouse of claim 1, wherein the mouse expresses Env protein in the lung tissue.

11. The mouse of claim 1, wherein the lung tissue of the mouse exhibits a higher level of phosphorylated p44/42 ERK than that of a non-transgenic control mouse.

12. A method for identifying a compound that affects tumorigenesis of human lung adenocarcinoma, comprising:
(a) administering a test compound to the transgenic mouse of claim 1, or to a lung tumor tissue or lung tumor cells isolated from said mouse; and
(b) evaluating the effect of the test compound on the onset of lung tumor formation, lung tumor cell growth, and/or lung tumor size to determine whether the compound affects tumorigenesis of human lung adenocarcinoma.

13. The method of claim 12, wherein step (b) evaluates whether the test compound delays the onset and/or suppresses the growth of the lung tumor in the mouse, the lung tumor tissue, and/or the lung tumor cells isolated from said mouse.

14. The method of claim 12, wherein step (b) comprises the step of analyzing and assessing histopathological sections of a lung tumor obtained from the mouse.

15. A method for identifying a compound that affects tumorigenesis of human lung adenocarcinoma, comprising:
(a) administering a test compound to the transgenic mouse of claim 5, or to a lung tumor tissue, or lung tumor cells isolated from said mouse; and
(b) detecting the levels of p44/42 ERK and phospho p44/42 ERK proteins in the lung of the transgenic mouse, the lung tumor tissue and/or the lung tumor cells isolated from the mouse to determine whether the test compound affects tumorigenesis of human lung adenocarcinoma.

16. The method of claim 15, wherein step (b) comprises the step of detecting the levels of p44/42 ERK and phospho p44/42 ERK proteins by western blotting, and/or detecting the expression level of p44/42 ERK mRNA by quantitative reverse transcription polymer chain reaction (RT-PCR).

17. A transgenic mouse whose genome comprises a Jaagsiekte sheep retrovirus (JSRV) envelope protein (Env)-encoding transgene operably linked to a surfactant protein C promoter (SPCp), wherein the lung tissue of the transgenic mouse expresses the transgene, and wherein the transgenic mouse develops a lung tumor by the age of 7 month and the lung tumor expresses the transgene, and further wherein the transgenic mouse has an FVB/N genetic background.

18. The transgenic mouse of claim 17, wherein the mouse develops a lung rumor by the age of 1 month.

19. A transgenic mouse whose genome comprises a Jaagsiekte sheep retrovinis (JSRV) envelope protein (Env)-encoding transgene operably linked to a surfactant protein C promoter (SPCp), wherein the lung tissue of the transgenic mouse expresses the transgene, and wherein the transgenic mouse develops a lung tumor by the age of 3 months and the lung tumor expresses the transgene, and further wherein the transgenic mouse has an FVB/N genetic background.

20. A method for identifying a compound that affects tumorigenesis of human lung adenocarcinoma, comprising:
(a) administering a test compound to the transgenic mouse of claim 17, or to a lung tumor tissue or lung tumor cells isolated from said mouse; and
(b) evaluating the effect of the test compound on the onset of lung tumor formation, lung tumor cell growth, and/or lung tumor size to determine whether the compound affects tumorigenesis of human lung adenocarcinoma.

* * * * *

SEQUENCE LISTING

```
<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: JSRV Env 1845 bp_F_primer

<400> SEQUENCE: 1
ttcccatgga tgccgaagcg ccgcgct                                           27

<210> SEQ ID NO 2
<211> LENGTH: 30
<212> TYPE: DNA
<213> ORGANISM: Artificial Sequence
<220> FEATURE:
<223> OTHER INFORMATION: JSRV Env 1845 bp_R_Primer

<400> SEQUENCE: 2
cttaagcttt cacgggtcgt cccccgcatc                                        30

<210> SEQ ID NO 3
<211> LENGTH: 24
<212> TYPE: DNA
<213> ORGANISM: Artificial Sequence
<220> FEATURE:
<223> OTHER INFORMATION: JSRV Env 252-725 bp Region_F-Primer

<400> SEQUENCE: 3
gcgtacattc ctgatccgcc aatg                                              24

<210> SEQ ID NO 4
<211> LENGTH: 24
<212> TYPE: DNA
<213> ORGANISM: Artificial Sequence
<220> FEATURE:
<223> OTHER INFORMATION: JSRV Env 252-725 bp Region_R_Primer

<400> SEQUENCE: 4
cggatgctgt cctcgatatt cagg                                              24

<210> SEQ ID NO 5
<211> LENGTH: 22
<212> TYPE: DNA
<213> ORGANISM: Artificial Sequence
<220> FEATURE:
<223> OTHER INFORMATION: JSRV Env 481-502 bp_F_Primer

<400> SEQUENCE: 5
cgagtgacta tctcaggcat tg                                                22
```

<210> SEQ ID NO 6
<211> LENGTH: 20
<212> TYPE: DNA
<213> ORGANISM: Artificial Sequence
<220> FEATURE:
<223> OTHER INFORMATION: JSRV Env 522-541 bp_R_Primer

<400> SEQUENCE: 6
tagtatgccc ttgcctagac                                              20

<210> SEQ ID NO 7
<211> LENGTH: 8
<212> TYPE: DNA
<213> ORGANISM: Artificial Sequence
<220> FEATURE:
<223> OTHER INFORMATION: Roch Universsal Probe set No. 48

<400> SEQUENCE: 7 actgggaa                                                            8

<210> SEQ ID NO 8
<211> LENGTH: 1848
<212> TYPE: DNA
<213> ORGANISM: Jaagsiekte sheep retrovirus (JSRV)

<400> SEQUENCE: 8
atgccgaagc gccgcgctgg attccggaaa ggctggtacg cgcggcagag gaactccctg      60
acgcatcaaa tgcaacgcat gacgctgagc gagcccacga gtgagctgcc cacccagagg     120
caaattgaag cgctaatgcg ctacgcctgg aatgaggcac atgtacaacc tccggtgaca     180
cctactaaca tcttgatcat gttattatta ttgttacagc gggtacaaaa tggggcagct     240
gcggcttttt gggcgtacat tcctgatccg ccaatgattc aatccttagg atgggataga     300
gaaatagtac ccgtatatgt taatgatacg agccttttag gaggaaaatc agatattcac     360
atttcccctc agcaagcaaa tatctctttt tatggcctta ccactcaata tcccatgtgc     420
ttttcttatc aatcgcagca tcctcattgt atacaggtat cagctgacat atcatatcct     480
cgagtgacta tctcaggcat tgatgaaaaa actgggaaaa atcatacgg gaacggatct     540 ggacccctcg acattccgtt ttgtgacaag catttaagca ttggcatagg catagacact     600
ccttggactt tatgtcgagc ccgggtcgca tcagtatata catcaataa tgccaatgcc     660 accttttat gggattgggc acctggagga cacctgatt ttcctgaata tcgaggacag     720
catccgccta ttttctctgt aaataccgct ccaatatacc aaacgaact atggaaactt     780 ttggctgctt ttggtcatgg caatagttta tatttacagc ccaatatcag tggaagcaaa     840
tatggtgatg taggagttac aggatttta tatcctcgag cttgcgtgcc gtatccattc     900
atgttgatac aaggccatat ggaaataaca ctgtcattaa atatttatca tttgaattgt     960
tctaactgca tactgactaa ttgtattagg ggagtagcca aaggagaaca ggttataata    1020
gtaaaacagc ctgcctttgt aatgctgccc gttgaaatag ctgaagcctg gtatgatgaa    1080
actgctttag aattattaca acgcattaat acggctctca gccgccctaa gagaggcctg    1140
agcctgatta ttttgggtat agtatcttta atcaccctca tagctacagc tgttacggct    1200
tccgtatctt tagcacagtc tattcaagct gcgcacacgg tagactcctt atcatataat    1260
gttactaaag tgatggggac ccaagaagat attgataaaa aaatagaaga taggctatca    1320
gctctatatg atgtagtcag agtcttagga gagcaagttc agagcattaa ttttcgcatg    1380
aaaatccaat gtcatgctaa ctataaatgg atttgtgtta caaaaaagcc atacaatact    1440

| | |
|---|---:|
| tctgattttc catgggacaa agtgaagaaa catttgcaag gaatttggtt caatactaat | 1500 |
| ctatcgttag accttttaca actgcataat gagattcttg atattgaaaa ttcgccgaag | 1560 |
| gctacactaa atatagccga tactgttgat aatttcttgc aaaatttatt ctctaatttt | 1620 |
| cctagtctcc attcgctgtg gaaaccctg attggtgtag aatacttgt gtttattata | 1680 |
| attgtcgtaa tccttatatt tccttgcctt gttcgtggca tggttcgcga ttttctaaag | 1740 |
| atgagagttg aaatgctgca tatgaaatat agaaatatgt tacagcacca acatcttatg | 1800 |
| gagcttttaa aaaataaaga gaggggagat gcggggacg acccgtga | 1848 |

```
<210> SEQ ID NO 9
<211> LENGTH: 3792
<212> TYPE: DNA
<213> ORGANISM: Homo sapiens

<400> SEQUENCE: 9
```

| | |
|---|---:|
| aagcttgaag actgctgctc tctaccacgt tagctcccct gtggcggagg atgactgtcc | 60 |
| taagagctca taggcacggg gcaaggggag cctggctgtc agctgcctgg gcttctagtc | 120 |
| ttgtgctttt tgcacaccag tccagggaac gaagaccact ggctttaaga tgcttcccca | 180 |
| gctgtcccca gactctgcca gcagggatt ctctggtctg agcttaagtt gtgttctccc | 240 |
| agccagggat gcccctgccc tttgatgtct ccttgctgcc acacatttag ccgccctccc | 300 |
| catgccagct tgggggagg gaagcagtga gggtagggag gtggctgggg cagctgggca | 360 |
| actgtcccca cccgtccctg gcacggctct gcccagtaca caagagcaa agtgaatctt | 420 |
| gtccccaccc ctgcagctga ggggctggag gaggaaacgg ggaggcccac acagaagggg | 480 |
| tggccaccgt ggggctgtcc atcactcagg gctctcagag ggagtcaacc cagaaacaga | 540 |
| caaagagggt gagtctgggc tgtgttctta gctagtgaga ggtcccctag aggatgaagt | 600 |
| agatgatgct aatgaggatg actggatgtc acacccatga tgctattagg tcctcataat | 660 |
| agcatagtga ggtggacagc tagtacctga cccatctcac agatgaacat actaatgcct | 720 |
| aacaaagcag aacgactcac gctgggtccc agagctggcc agtggaagca ctgagacctc | 780 |
| cacatactga aggcatggac tattgaccgc tgttggtatt ggtctcatca ttgactatca | 840 |
| ttaagtgttg gctgtttgca tgcttcctgc ccagtggcag gttcaaagaa gcccgcagga | 900 |
| agcgtgctcc tttctttccc agggcccgca attgggctgg aagatagagc aacaaaaagc | 960 |
| gcccatgtaa ctcatgggaa cattcatgtg tgctgaatgg caggtgaagg tgccacagag | 1020 |
| aggctgagga tttcagaggg caccatgaac tggagtgagg tcgcagagca ggtgccattg | 1080 |
| gctcttggcc tgtttgggtg ggtggcattc agagaggtgg aaggtcagat gcactgttca | 1140 |
| cgcctgtaat ctcagcactt tggaaggcca aggtaggagg atcacacgag gccaggagat | 1200 |
| caacgctgca gtgagctatg aagctgtgat tgcaccactg cactccagct ggggtaacag | 1260 |
| agtgagaccc tgtctctaaa taattaaata aataaaataa aaataaaacc ggagaagtgg | 1320 |
| agagggattg gaggtgggct ttcacagagg gagaaacggc ttaagtacag gccaaaaagt | 1380 |
| gagaaggctg cagacagggc tggtaggggg aggggaagt ttggcacacc cagctaaagg | 1440 |
| tccttctgtg tctccttctc caaggaaccc aagaccttca cttggttggt gtgagcactc | 1500 |
| caggaggcag gcaccctccc tcagccctca agcaagcaaa aatgggttta aaaaagaag | 1560 |
| gagaagaagc agcagcagca gccgccacag agcttgtgac agctacagcc taagggcaac | 1620 |
| aggcagggga gaccaaggac cagaaagagc agaggctttt tcaaagaaag agatccctct | 1680 |
| cccagcaccc agcgatggcg gcaaacccca cccacagtgc ctgctaagaa caagtcccac | 1740 |

```
gtgagaacaa catggccccc cgagatgccc acagggaccc cgagatgcct gcagtgcttg    1800
gctctcccgc tggccagctg cccacctggc tcaggcccag tactcgtgag tcagccgatc    1860
aatcccaatg ttgccaggat gatggggcg ggagtaaggg ccctggggga gggcaggggt    1920
gggcactgca ggcgagctgt ctcccacatc tggcacctgc acacagctga ggccgagctg    1980
agaggatgct tctgtgggct cccctcctc ccggcacccc tcccctcctt tcactgtcct    2040
aggacactct ctggctgctg gagtcttagg caaatattta aggggcagc aaggggtga    2100
ggagggtggt gggagcaaac acttccctcc ctttcttcct ccctgcgctt ctcaggggct    2160
ctcagttcag atgccatgct gttatgcaac cttggggctg aaggccctcc agatggagag    2220
ggggacaggg gaacctgcca gctcatgacc gaagggcagg gcccaggtgg gaggggctg    2280
gggcagggga caggaactgg ggtggcatgt taaaggacag gaggctggtt gggcatggtg    2340
gctcacacct gtaatcctag cactttagga ggccgagatc acttgagccc aggagttcaa    2400
gaccagcctg ggcaacatgg tgaaaactca tctctataaa acaagcaaaa attagctggg    2460
cacaatggca tgcactggta gtcccagcta cttgggatgc tgaggtgtga ggatcaccgg    2520
agtccaggag gtcaacgctg cagtgagcag tgatctcgct actgcatgcc agcctgggtg    2580
ataaagtgag accctgtctc acaacaaaac aaaacaaaac aaaacaaaag gataggaggt    2640
taagggagcg agcccaggcc tggactctgc cacagtcacc tgagtttaga ggtgaaggga    2700
ctttagagac cacctggccc aaggagtgaa agggaacctg agagaaaggg tgagccagcc    2760
caaagtcatt ggcagatttg acctcgtaaa tacatagaga tggctttggg aaggcactag    2820
gaaagacaga gaaaagagaa ggagacagtc ctcaaagctg atcgtatttg ggtgagtatt    2880
attctcaggg caaatttagg atcagaggat gcagaaaggg gagtctagag gggtagagtg    2940
tagaccacag ggtgagtgag ctgattcgag gatggggaga ctgggagccc accagtgacc    3000
agagccagcc ctgttcaggg ctgtccgggc agaagaaagc agtgtcagac ctggaatctg    3060
ccatcagcac agcctgcaat tgacagacaa gcccagagca aagaaggaag cactgcacat    3120
gagtaagagc ttgccaccag tggggacaga gtttccagaa ttaggaaaat aatcactggg    3180
ggcaagtttg aggttggtac cagatatgtg ggaggaggca aggtaaggga aagagtactt    3240
gaagttggaa ctggtccttg cagggaaatg cacatttatg aaacccgaa aactgatgtc    3300
aaagcacctc ctgccttggg cagagtcctc tcagagtcta caggtgctgc ctccagaacc    3360
ctcttcctgg agcgcatccc tatgtatcta gaaattctgc tgggaaatat gatggtcaga    3420
cccttggcca cctgaaaggt tcagggtggt agaagaaaaa ggaaagccac agggcagcag    3480
gggcaggtgc cagcaaggaa ggcaggcacg ccaggaagac acccatggtg agaagtgcag    3540
atgcccgag ggcaagtttg ctcaactcac ccaggtttgc tcttgctggg gccaagagga    3600
ctcatgtgcc agggccaagg gcccttgggg gctctcacag ggggcttatc tgggcttcgg    3660
ttctggaggg ccaggaacaa acaggcttca aagccaaggg cttggctggc acacagggg    3720
cttggtcctt cacctctgtc ccctctccct acggacacat ataagaccct ggtcacacct    3780
gggagaggag ga                                                        3792
```